(12) United States Patent
Galen et al.

(10) Patent No.: US 6,778,852 B2
(45) Date of Patent: Aug. 17, 2004

(54) COLOR-CODED ECG (75) Inventors: Peter M. Galen, Portland, OR (US); Damon J. Coffman, Portland, OR (US); Robert A. Warner, Tigard, OR (US)

(73) Assignee: Inovise Medical, Inc., Newberg, OR (US)

( * ) Notice: Subject to any disclaimer, the term of this patent is extended or adjusted under 35 U.S.C. 154(b) by 0 days.

(21) Appl. No.: 10/389,649

(22) Filed: Mar. 13, 2003

(65) Prior Publication Data

US 2003/0176802 A1 Sep. 18, 2003

Related U.S. Application Data

(60) Provisional application No. 60/364,404, filed on Mar. 14, 2002.

(51) Int. Cl.[7] .................................................. A61B 5/04
(52) U.S. Cl. ..................................................... 600/523
(58) Field of Search ................................... 600/523–525

(56) References Cited

U.S. PATENT DOCUMENTS

| | | | |
|---|---|---|---|
| 4,974,598 A | | 12/1990 | John |
| 5,540,232 A | * | 7/1996 | Laney et al. ................ 600/510 |
| 6,389,308 B1 | * | 5/2002 | Shusterman ................ 600/509 |

* cited by examiner

*Primary Examiner*—Mark Bockelman
(74) *Attorney, Agent, or Firm*—Jon M. Dickinson, P.C.; Robert D. Varitz, P.C.

(57) ABSTRACT

A method and system for presenting time-based, comparative, patient-specific ECG data in various presentation formats, wherein color-coding is employed as a visual device to communicate vividly different, selected "changed" characteristics in that patient's current ECG-detected status.

7 Claims, 9 Drawing Sheets

(8 of 9 Drawing Sheet(s) Filed in Color)

Lead aVF
Colors *In* the Tracing Refer To Amplitudes
Colors *Above* the Tracing Refer to Durations

Fig. 4

| Figure - Standard Sequence of Limb Leads - Acute IMI | | | | | | | | |
|---|---|---|---|---|---|---|---|---|
| | Q | Q | R | S | ST | T | PR | QRS | QTc |
| Lead | Dur. | Ampl. | Ampl. | Ampl. | Ampl. | Ampl. | Dur. | Dur. | Dur |
| I | # | # | # | # | | # | # | # | # |
| II | # | # | # | # | | # | # | # | # |
| III | # | # | # | # | | # | # | # | # |
| aVR | # | # | # | # | # | # | # | # | # |
| aVL | # | # | # | # | | # | # | # | # |
| aVF | # | # | # | # | | # | # | # | # |
| V1 | # | # | # | # | # | # | # | # | # |
| V2 | # | # | # | # | # | # | # | # | # |
| V3 | # | # | # | # | # | # | # | # | # |
| V4 | # | # | # | # | # | # | # | # | # |
| V5 | # | # | # | # | # | # | # | # | # |
| V6 | # | # | # | # | # | # | # | # | # |

Fig. 5

Figure - Cabrerra Sequence of Limb Leads - Acute IMI

| Lead | Q Dur. | Q Ampl. | R Ampl. | S Ampl. | ST Ampl. | T Ampl. | PR Dur. | QRS Dur. | QTc Dur |
|------|--------|---------|---------|---------|----------|---------|---------|----------|---------|
| aVL  | # | # | # | # |   | # | # | # | # |
| I    | # | # | # | # |   | # | # | # | # |
| -aVR | # | # | # | # | # | # | # | # | # |
| II   | # | # | # | # | # | # | # | # | # |
| aVF  | # | # | # | # | # | # | # | # | # |
| III  | # | # | # | # | # | # | # | # | # |
| V1   | # | # | # | # | # | # | # | # | # |
| V2   | # | # | # | # | # | # | # | # | # |
| V3   | # | # | # | # | # | # | # | # | # |
| V4   | # | # | # | # | # | # | # | # | # |
| V5   | # | # | # | # | # | # | # | # | # |
| V6   | # | # | # | # | # | # | # | # | # |

Fig. 6

Figure - Standard Sequence of Limb Leads - LVE

| Lead | Q Dur. | Q Ampl. | R Ampl. | S Ampl. | ST Ampl. | T Ampl. | PR Dur. | QRS Dur. | QTc Dur |
|------|--------|---------|---------|---------|----------|---------|---------|----------|---------|
| I    | # | # | # | # | # | # | # | # | # |
| II   | # | # | # | # | # | # | # | # | # |
| III  | # | # | # | # | # | # | # | # | # |
| aVR  | # | # | # | # | # | # | # | # | # |
| aVL  | # | # | # | # | # | # | # | # | # |
| aVF  | # | # | # | # | # | # | # | # | # |
| V1   | # | # |   | # | # | # | # | # | # |
| V2   | # | # |   | # | # | # | # | # | # |
| V3   | # | # | # | # | # | # | # | # | # |
| V4   | # | # | # | # | # | # | # | # | # |
| V5   | # | # | # | # |   | # | # | # | # |
| V6   | # | # | # | # |   | # | # | # | # |

Fig. 7

Figure -Standard Sequence of Limb Leads --
Increased QTc Dispersion

| Lead | Q Dur. | Q Ampl. | R Ampl. | S Ampl. | ST Ampl. | T Ampl. | PR Dur. | QRS Dur. | QTc Dur |
|------|--------|---------|---------|---------|----------|---------|---------|----------|---------|
| I    | #      | #       | #       | #       | #        | #       | #       | #        | #       |
| II   | #      | #       | #       | #       | #        | #       | #       | #        | #       |
| III  | #      | #       | #       | #       | #        | #       | #       | #        | #       |
| aVR  | #      | #       | #       | #       | #        | #       | #       | #        | #       |
| aVL  | #      | #       | #       | #       | #        | #       | #       | #        | #       |
| aVF  | #      | #       | #       | #       | #        | #       | #       | #        | #       |
| V1   | #      | #       | #       | #       | #        | #       | #       | #        | #       |
| V2   | #      | #       | #       | #       | #        | #       | #       | #        | #       |
| V3   | #      | #       | #       | #       | #        | #       | #       | #        | #       |
| V4   | #      | #       | #       | #       | #        | #       | #       | #        | #       |
| V5   | #      | #       | #       | #       | #        | #       | #       | #        | #       |
| V6   | #      | #       | #       | #       | #        | #       | #       | #        | #       |

Fig. 8

Figure - Standard Sequence of Limb Leads -- Acute Pericarditis

| Lead | Q Dur. | Q Ampl. | R Ampl. | S Ampl. | ST Ampl. | T Ampl. | PR Dur. | QRS Dur. | QTc Dur |
|------|--------|---------|---------|---------|----------|---------|---------|----------|---------|
| I    | #      | #       | #       | #       | #        | #       | #       | #        | #       |
| II   | #      | #       | #       | #       | #        | #       | #       | #        | #       |
| III  | #      | #       | #       | #       | #        | #       | #       | #        | #       |
| aVR  | #      | #       | #       | #       | #        | #       | #       | #        | #       |
| aVL  | #      | #       | #       | #       | #        | #       | #       | #        | #       |
| aVF  | #      | #       | #       | #       | #        | #       | #       | #        | #       |
| V1   | #      | #       | #       | #       | #        | #       | #       | #        | #       |
| V2   | #      | #       | #       | #       | #        | #       | #       | #        | #       |
| V3   | #      | #       | #       | #       | #        | #       | #       | #        | #       |
| V4   | #      | #       | #       | #       | #        | #       | #       | #        | #       |
| V5   | #      | #       | #       | #       | #        | #       | #       | #        | #       |
| V6   | #      | #       | #       | #       | #        | #       | #       | #        | #       |

Fig. 9

Figure - Standard Sequence of Limb Leads - LBBB

| Lead | Q Dur. | Q Ampl. | R Ampl. | S Ampl. | ST Ampl. | T Ampl. | PR Dur. | QRS Dur. | QTc Dur |
|------|--------|---------|---------|---------|----------|---------|---------|----------|---------|
| I    |        |         | #       | #       |          |         | #       |          | #       |
| II   | #      | #       | #       | #       | #        | #       | #       |          | #       |
| III  | #      | #       | #       | #       | #        | #       | #       |          | #       |
| aVR  | #      | #       | #       | #       | #        | #       | #       |          | #       |
| aVL  |        |         | #       | #       |          |         | #       |          | #       |
| aVF  | #      | #       | #       | #       | #        | #       | #       |          | #       |
| V1   | #      | #       | #       | #       | #        | #       | #       |          | #       |
| V2   | #      | #       | #       | #       | #        | #       | #       |          | #       |
| V3   | #      | #       | #       | #       | #        | #       | #       |          | #       |
| V4   | #      | #       | #       | #       | #        | #       | #       |          | #       |
| V5   |        |         | #       | #       |          |         | #       |          | #       |
| V6   |        |         | #       | #       |          |         | #       |          | #       |

Fig. 10

Figure - Standard Sequence of Limb Leads - Old AMI

| Lead | Q Dur. | Q Ampl. | R Ampl. | S Ampl. | ST Ampl. | T Ampl. | PR Dur. | QRS Dur. | QTc Dur |
|------|--------|---------|---------|---------|----------|---------|---------|----------|---------|
| I    | #      | #       | #       | #       | #        | #       | #       | #        | #       |
| II   | #      | #       | #       | #       | #        | #       | #       | #        | #       |
| III  | #      | #       | #       | #       | #        | #       | #       | #        | #       |
| aVR  | #      | #       | #       | #       | #        | #       | #       | #        | #       |
| aVL  | #      | #       | #       | #       | #        | #       | #       | #        | #       |
| aVF  | #      | #       | #       | #       | #        | #       | #       | #        | #       |
| V1   | #      |         |         | #       | #        | #       | #       | #        | #       |
| V2   | #      |         |         | #       | #        | #       | #       | #        | #       |
| V3   | #      |         |         | #       | #        | #       | #       | #        | #       |
| V4   | #      | #       | #       | #       | #        | #       | #       | #        | #       |
| V5   | #      | #       | #       | #       | #        | #       | #       | #        | #       |
| V6   | #      | #       | #       | #       | #        | #       | #       | #        | #       |

Fig. 11

Figure — Standard Sequence of Limb Leads - LAHB

| Lead | Q Dur. | Q Ampl. | R Ampl. | S Ampl. | ST Ampl. | T Ampl. | PR Dur. | QRS Dur. | QTc Dur |
|---|---|---|---|---|---|---|---|---|---|
| I | # | # | # | # | # | # | # | # | # |
| II | # | # |   |   | # | # | # | # | # |
| III | # |   |   |   | # | # | # | # | # |
| aVR | # | # | # | # | # | # | # | # | # |
| aVL | # | # | # | # | # | # | # | # | # |
| aVF | # | # |   |   | # | # | # | # | # |
| V1 | # | # | # | # | # | # | # | # | # |
| V2 | # | # | # | # | # | # | # | # | # |
| V3 | # | # | # | # | # | # | # | # | # |
| V4 | # | # | # | # | # | # | # | # | # |
| V5 | # | # | # | # | # | # | # | # | # |
| V6 | # | # | # | # | # | # | # | # | # |

Fig. 12

Fig. — Monitoring for Ischemia - 24 Hour Display
March 4 to March 5, 2000

Colors = Maximum Severity of ST Deviation

| 10 AM | 11 AM | 12 AM | 1 PM | 2 PM | 3 PM | 4 PM | 5 PM | 6 PM | 7 PM | 8 PM | 9 PM |
|---|---|---|---|---|---|---|---|---|---|---|---|

| 10 PM | 11 PM | 12 AM | 1 AM | 2 AM | 3 AM | 4 AM | 5 AM | 6 AM | 7 AM | 8 AM | 9 AM |
|---|---|---|---|---|---|---|---|---|---|---|---|

Fig. 13

Fig. — Monitoring for Ischemia - 1 Hour Display
March 4, 2000 - 6:00 to 7:00 PM

Colors = Maximum Severity of ST Deviation

| 6:00 PM | 6:05 PM | 6:10 PM | 6:15 PM | 6:20 PM | 6:25 PM |
|---|---|---|---|---|---|

| 6:30 PM | 6:35 PM | 6:40 PM | 6:45 PM | 6:50 PM | 6:55 PM | 7:00 PM |
|---|---|---|---|---|---|---|

Figure – Example of Monitoring of Multiple Physiological Parameters

Fig. 16

COLOR-CODED ECG

CROSS-REFERENCE TO RELATED APPLICATION

The application claims priority to U.S. Provisional Patent Application Serial No. 60/364,404, filed Mar. 14, 2002, entitled "Color-Coded ECG". The entire content of that currently co-pending provisional patent application is hereby incorporated herein by reference.

INTRODUCTION

Fundamentally what is proposed by this invention is a system and a method for selectively color marking certain regions in acquired, time-domain ECG data, such as in acquired, time-based ECG waveform data, for the purpose of comparing this data with previously acquired such data, all for the purpose of detecting and highlighting changes, variations, anomalies, etc., that can best be seen in a comparative mode for analysis. In particular, what we envision is a color-coded presentation wherein regions of ECG data can clearly be seen for selected content in a manner which displays time-based highlighting utilizing various colors. The comparison referred to might take the place, for example, between a patient's current ECG waveform and an earlier-taken ECG waveform. Another comparison which might be made is between a patient's current ECG waveform and an average, or standard, ECG waveform, such as one which is known to reflect, for example, the ECG waveform norm for a particular group in a population.

Color coding is preferably accomplished utilizing print, electronic or other appropriate media, or presentation formatting, which permits traditional "rainbow chrominance" display. However, as employed herein we intend the concept of color coding additionally to include appropriate, distinguishable grey-scale coding in settings where "black-and-white" only presentation media, etc., is/are available.

Regarding the manner in which output information is provided by this invention, color coding may not only be used in the body of a graphically presented ECG waveform per se, but may also be similarly employed in table, matrix, chart and/or timeline presentations of data. All of these kinds of presentations are clearly described and illustrated in the text and drawings herein. Color-coded, or marked, output information can also be presented, in accordance with the invention, following certain applications of statistical analyses, the results of which can be immediately grasped visually because of color coding. On a time-based basis, in accordance with practice of the present invention, color coding, or marking, can vividly show at a single glance heart-behavior parameters as they change in time.

The various special features and color-visual advantages that are offered by the present invention will become more fully apparent as the description which now follows is read in conjunction with the accompanying drawings.

DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Figure 1:
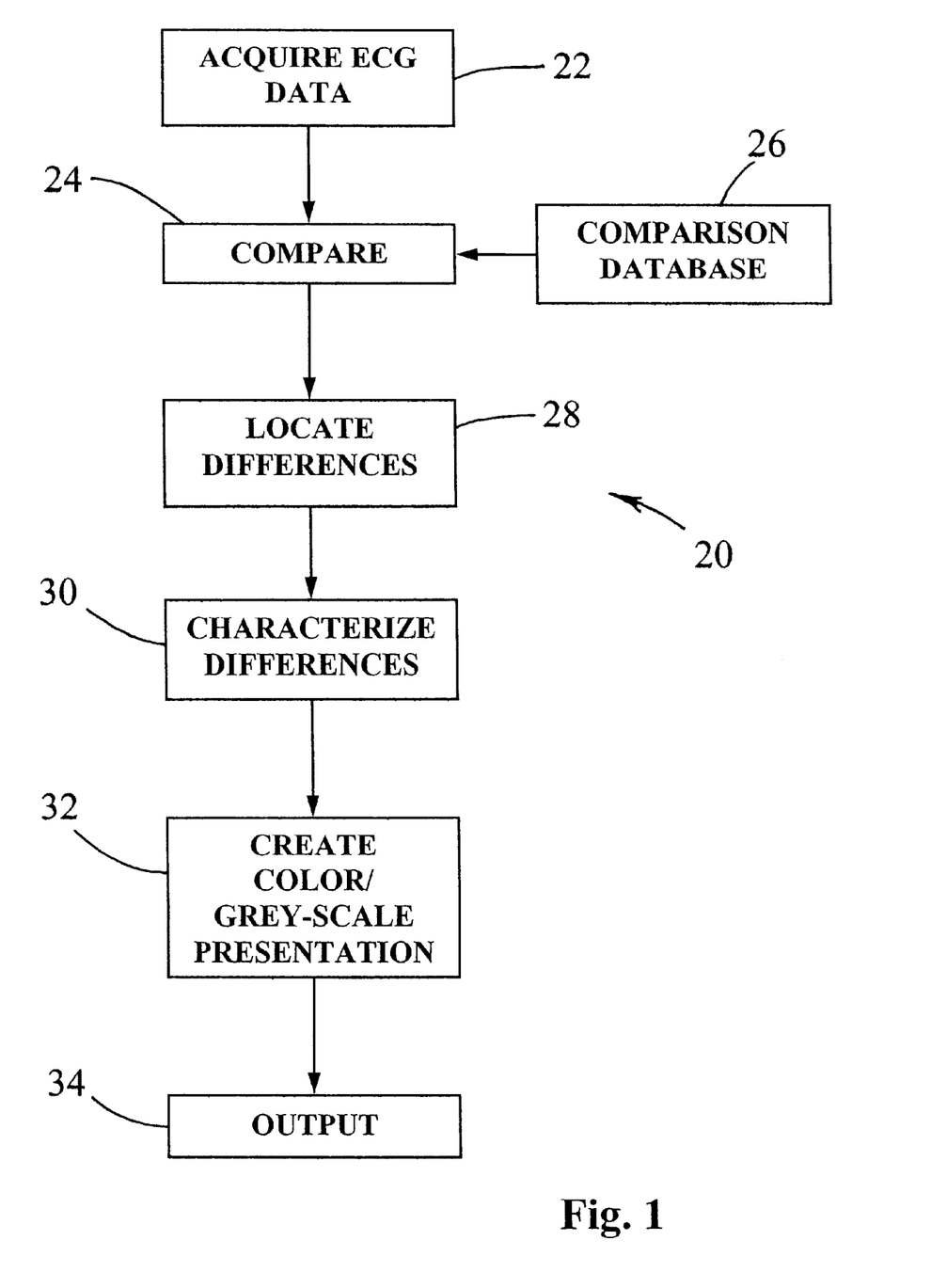
FIG. 1 is a block/schematic diagram illustrating both the system and the methodology of a preferred embodiment of, and of a preferred and best mode manner of practicing, the present invention.
Figure 2:
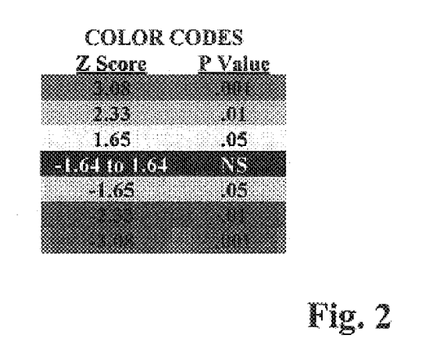
FIG. 2 is a color-code chart which relates colors that are employed in various other ones of the drawings herein to certain value parameters that are relevant to the respective manners in which these colors are employed in the drawings.

Turning first of all to FIGS. 1 and 2 in drawings, FIG. 1 illustrates in block/schematic form generally at 20 both the structural systemic layout, and the preferred and best mode manner of practicing the methodology, of the present invention. Shown in FIG. 1 are an ACQUIRE ECG DATA block 22, a COMPARE block 24, a COMPARISON DATABASE block 26, a LOCATE DIFFERENCE block 28, a CHARACTERIZE DIFFERENCES block 30, a CREATE COLOR/GREY-SCALE PRESENTATION block 32, and an OUTPUT block 34.

Block 22 is also referred to herein as input structure. Blocks 24, 28, 30 collectively are referred to herein also as comparison structure. Within this collection of three blocks, block 30 represents structure and methodology wherein selected statistical analyses are performed. Block 26 constitutes an available, previously established, relevant ECG data base. Blocks 32, 34 are also referred to in system 20 as color-coding and output structure.

In a manner of describing both the systemic and methodologic organization of this invention in relation to what is shown in FIG. 1, and describing these aspects of the invention from a methodologic point of view with respect to this figure, practice of the invention involves (a) the acquisition for examination and study of current, time-based ECG data from a patient, (b) the comparing of portions of that data, i.e., whatever portions are deemed to be the most appropriate, to related parts of an existing database of similar data previously developed either from the same patient, or from an appropriate, normalized collection of data derived from a selected group of people in the population, (c) as a consequence of that comparing activity, locating regions in currently-acquired data which suggest notable changes and/or variations found during the comparison activity, (d) further, and also on the basis of that comparing activity, performing, for example, a statistical analysis which will characterize noted differences in, for example, statistical standard-deviation terminology and various numeric values, and (e) the creation and outputting, through selection and assignment, of an output, time-based presentation data-stream wherein different, specially noted features are highlighted with different selected colors. This output, color-coded data-stream can be enabled selectively to produce printed document material, display screen material, etc., wherein, either in graphical and/or tabular and/or numeric and/or word-literature form, comparison information is visually colored to describe vividly and unambiguously for a reviewer areas of heart-performance change and variation which are considered to be of importance and/or general interest.

From this overall description which has just been given regarding how the methodology of the present invention flows generally from beginning to ending with respect to the treatment of a particular collection of fresh ECG data gathered from a patient, and from the more detailed description which now follows below further elaborating these performance features of the invention, those of general skill in the art will recognize that practice of the invention is relatively easily implemented utilizing modern computer and data-processing hardware, armed with various algorithms of many different selectable designs that are effective to implement the steps of the invention. Because of this, no detailed description is provided herein with respect to any particular algorithmic approach employed within any particular or specific piece of specific equipment, inasmuch as neither of these things forms any part per se of the present invention.

FIG. 2 presents a color key, or legend, which describes, in a rainbow-chrominance vertical stack of different colors, decorated with certain numeric values, just how other ones of the drawings herein, still to be described, can be read graphically and especially visually-informatively with the aid of these colors.

BACKGROUND AND RATIONALE

When electrocardiographers interpret an ECG, their basic task is to judge whether the tracing that they're reviewing differs in one or more ways from normal. For example, is a Q-wave in a particular lead deep or wide enough to be considered pathological, or is it sufficiently small to suggest that it is merely a variant of normal? Similarly, is an R-wave in a given lead tall enough to diagnose left ventricular enlargement, or is it within the expected range for an individual of that gender and age?

Presumably, with increasing experience, an electrocardiographer's judgment regarding such questions becomes more reliable. However, even the most expert electrocardiographers cannot legitimately claim infallibility in this regard. Also, in many clinical situations, a highly skilled electrocardiographer isn't available. The present invention addresses these issues by determining, visually, and in color, which, if any, portions of the ECG complex differ significantly from an empirically established normal standard.

STATISTICAL BASIS OF THE INVENTION

At each interval of sampling, one can express the difference between an individual patient's recorded voltage and the mean voltage of a population of patients as what is known as a standard-score. The standard score expresses such a difference in units of the standard deviation of the population to which the individual is being compared:

Standard-Score=(Patient's Value−Mean of Population)/Standard Deviation of the Population For example, if the mean and the standard deviation at a given interval of sampling were 100- and 50-microvolts, respectively, an individual who has 200-microvolts at that interval of sampling would have a standard score-of 2.0. A different individual who had 25-microvolts at that interval of sampling would have a standard-score of −1.5. Expressing these differences as standard-scores has several advantages. The most important one in this context is that when the data are normally distributed, one can use widely available statistical tables convert the standard-scores directly into the probability that the individual's value is statistically significantly above or below the mean of a given population. For instance, if the standard-score is 1.65, then the patient's value exceeds that of the mean value at a P-value of $\leq 0.05$. If the standard-score is −2.33, the patient's value is less than the mean value at a P-value of $\leq 0.01$. We have demonstrated, in several, different, prepared databases, that the values of the voltages recorded by ECG machines have Gaussian distributions.

Applications of the Methodology of the Invention

The versatility, and the significant communicative advantages, offered by the present invention and its practice will now be discussed and illustrated in detail in relation to a number of specific, "real-life" examples showing how color-coded ECG data, presented in various different ways, makes important, cardio-related information about a person's heart vividly stand out for notice and attention.

1. The Resting Electrocardiogram

Analog Tracings

It has recently been shown that, for diagnosing healed inferior MI, standard-scores are superior (a) to raw voltage scores, (b) to the durations of Q-waves, and (c) to the interpretations by an experienced electrocardiographer of an analog ECG waveform. In this setting, one important purpose of the proposed, color-coded ECG is to indicate to the reader, precisely which portions of a patient's ECG are statistically significantly different from an empirically established normal standard.

Figure 3:
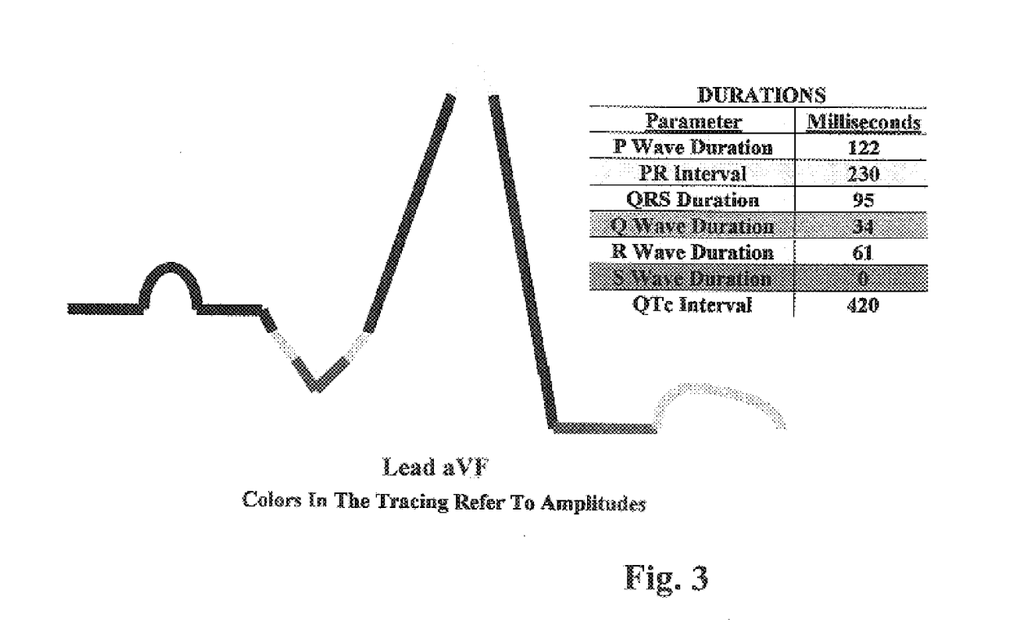
FIG. 3 shows a color-coded, analog, ECG waveform prepared in accordance with practice of the present invention.
Figure 4:
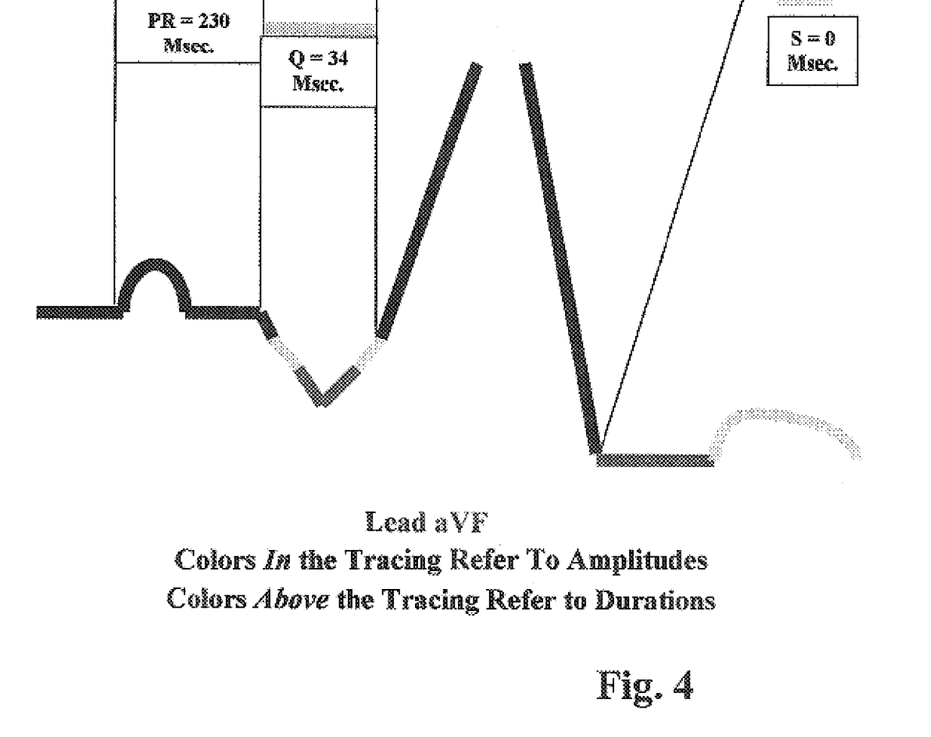
FIG. 4 illustrates another graphical color-coded waveform prepared in accordance with practice of the invention.

FIGS. 3–12, inclusive, in the drawings exemplify the above principles and findings in the resting ECG. FIGS. 3 and 4 show alternative types of time-based analog displays of a color-coded ECG, and FIGS. 5–12, inclusive, demonstrate how color-coding can augment a digital representation for ECG data regarding various diagnoses. In the figures, the legends show seven different colors, along with the respective standard-scores and associated P-values that correspond to each of them. As a aid to an interpreter regarding what the illustrated sequence of colors represents, the specific selection of colors presented herein for illustration purposes is based on the Doppler spectrum: As the standard-scores increase, the colors shift toward the red end of the spectrum, and as they decrease, the colors shift toward the violet end. An exception to the colors of the Doppler spectrum employed herein is that, for the portions of the ECG data that do not differ significantly from normal, the chosen color is black, rather than green. Standard-scores for each interval of sampling are calculated using the means, and the standard deviations, of the pooled data of a large group of clinically, or angiographically, normal individuals. It should be understood that while a specific pattern of color coding is illustrated herein, other patterns could just as well be chosen and employed.

FIG. 3 presents an analog tracing showing that the associated patient has an abnormally deep Q-wave that becomes even more abnormal near its nadir. It also shows that the peak of the R-wave is abnormally tall, that the ST-segment is very significantly depressed, and that the entire T-wave is significantly lower than normal. The table located above the T-wave shows that the durations of several parts of the tracings are also significantly abnormal. Specifically, the PR-interval and the duration of the Q-wave are abnormally long. Conversely, the table indicates that the S-wave is abnormally short—in this case absent. The time-changing, or differentiating, colors which mark different respective portions of the Q-wave demonstrate a powerful capability of the present invention to highlight time-changing matters which are of importance in evaluating heart behavior.

FIG. 4 presents the same kind of analog display of abnormalities of amplitude as does FIG. 1. However, rather than listing the abnormalities of duration in a table, this display shows the informative use of vertical and oblique lines that abut the analog tracing.

Digital Data

The color-coded digital displays consist of matrices of data in which each row represents a different lead, and each column (time-based) shows an ECG parameter. The cells that are statistically significantly greater than or less than a normal standard are colored using the same system of codes used for the analog tracings. These matrices are intended to augment, rather than replace, the standard analog ECG tracing. For example, if all the cells of a given matrix are black and white, the reader can instantly conclude that no part of the patient's ECG is significantly abnormal in any lead. Also, if the reader suspects that a certain portion of a patient's ECG is abnormal in one or more leads, that reader can examine the matrix to determine if such an impression is correct.

In FIGS. 3–10, inclusive, the symbol "#" stands for any number that would be appropriate for the parameter in question. Also, in each colored cell of the matrix, the color represents the maximum deviation of the parameter from normal. For example, if a cell that contains the data from a T-wave is orange, at least part of that T-wave would be orange, but other portions of the T-wave in the same lead that are less markedly abnormal would be yellow.

Figure 5:
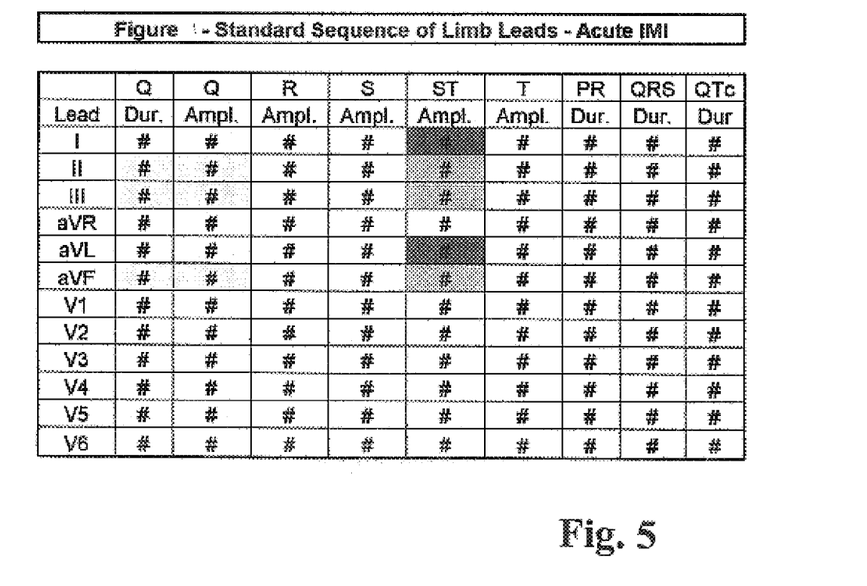
FIGS. 5–12, inclusive, illustrate different tabular, and/or chart, and/or matrix-style, color-coded data presentations which have been produced in accordance with practice of the present invention.

FIG. 5 relates to an acute inferior MI, and here, the matrix shows that the Q-waves in leads II, III and aVF are abnormally wide and deep, and that the ST-segments are abnormally elevated in the same leads. In addition there is "reciprocal" depression of the ST-segments in leads I and aVL.

Figure 6:
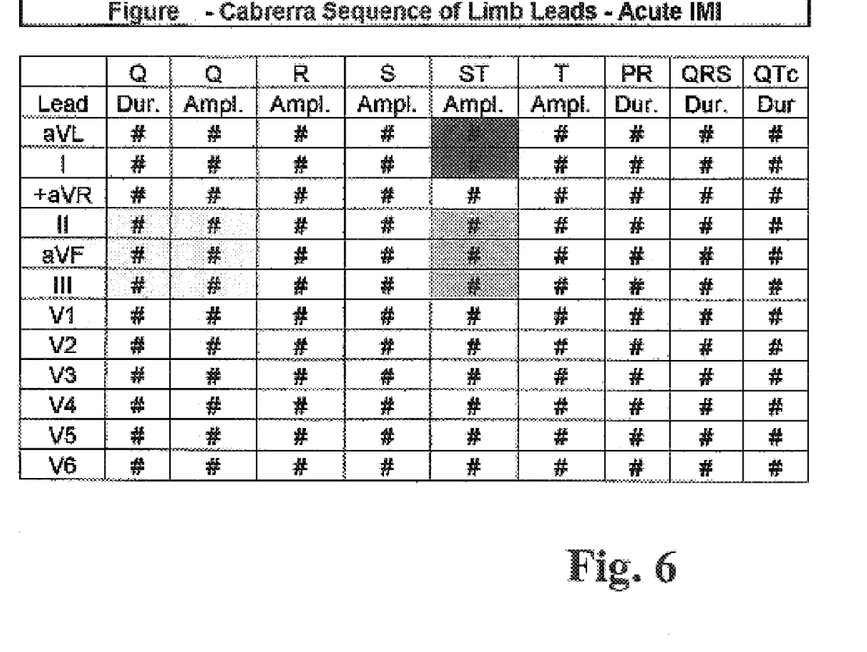

FIG. 6 shows the same data as does FIG. 5. However, by displaying here the data of the limb leads in the Cabrerra sequence, it more easily demonstrates the concordance of the changes in contiguous leads.

Figure 7:
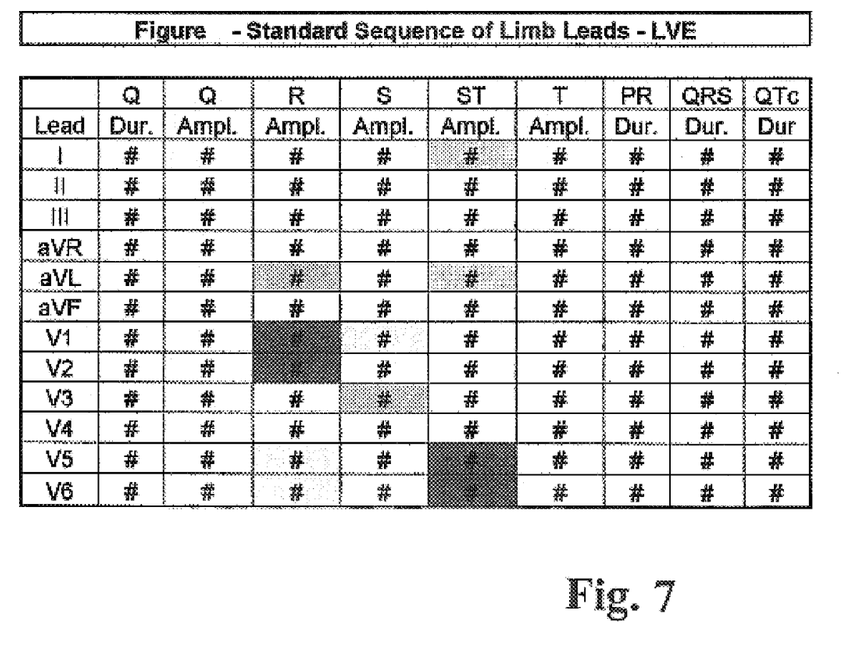

FIG. 7 presents a matrix which shows features typical of left ventricular enlargement. The R-waves area abnormally tall in leads aVL and V5 and V6, and are diminished in leads V1 and V1. The S-waves are abnormally deep in leads V1 and V3, and the ST-segments are significantly depressed in leads I, aVL, V5 and V6.

Figure 8:
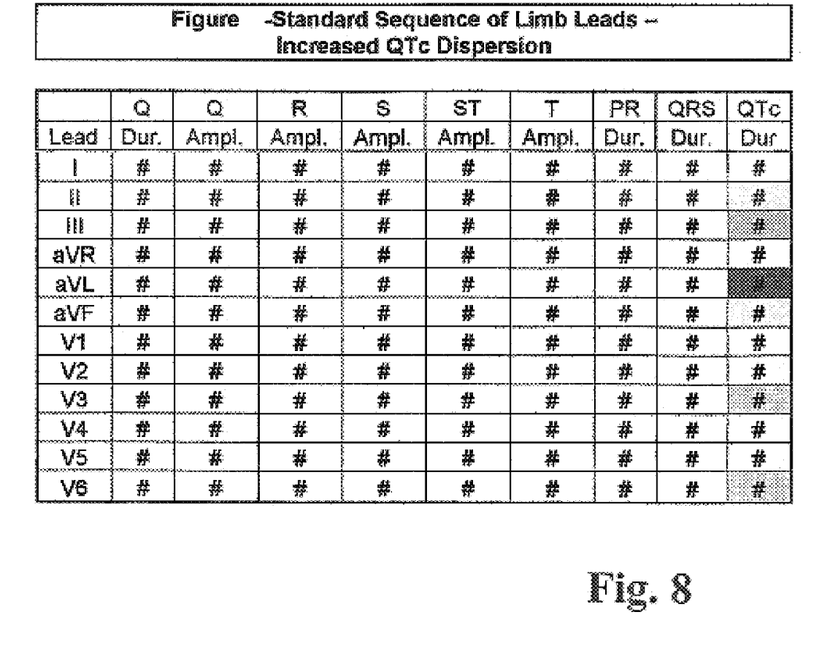

In FIG. 8, the last column of the matrix shows significant variation of the QTc among the twelve leads.

Figure 9:
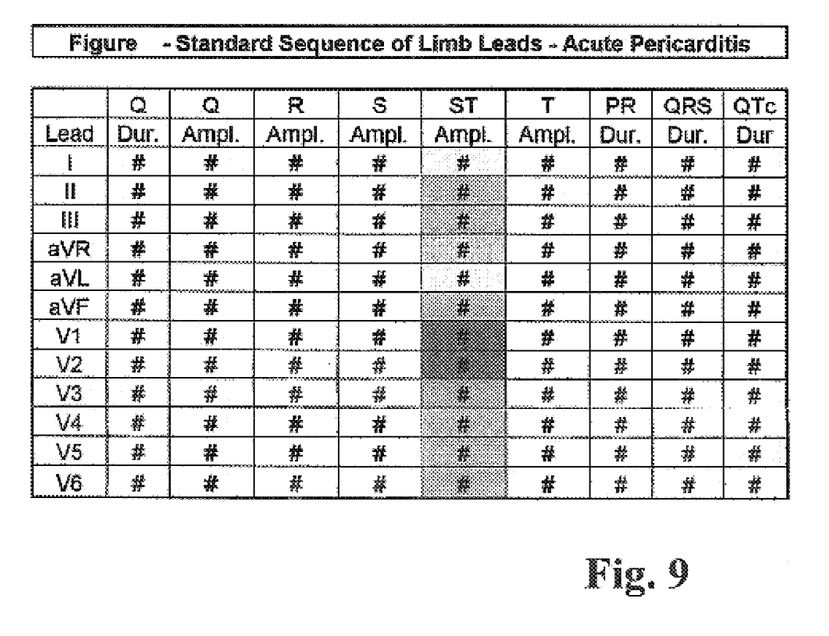

Shown in FIG. 9, in eleven of the twelve leads, the ST-segments are abnormally elevated. This is typical of acute pericarditis, rather than epicardial ischemia, since the elevations of the ST-segments are not confined to contiguous leads.

Figure 10:
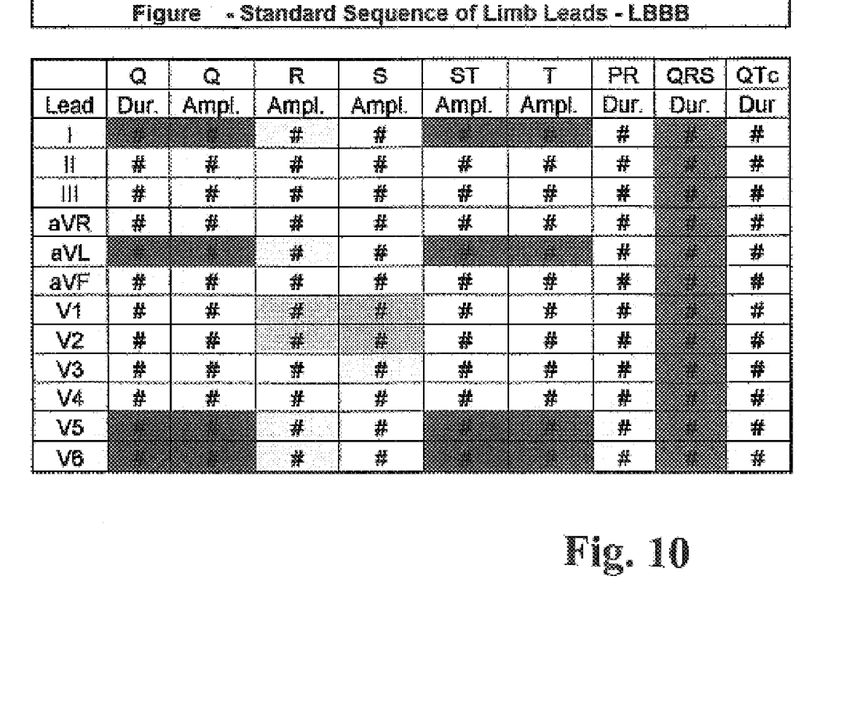

In FIG. 10, the matrix shows features typical of left bundle branch block. The duration of the QRS is markedly prolonged in all twelve leads. Because of activation of the interventricular septum form right to left, Q-waves in leads I, aVL, V5 and V6 are absent or greatly diminished. The amplitudes of the R-waves are increased in the "lateral leads" and decreased in the right precordial leads. The ST-segments are depressed and the T-waves inverted in leads I, aVL, V5 and V6.

Figure 11:
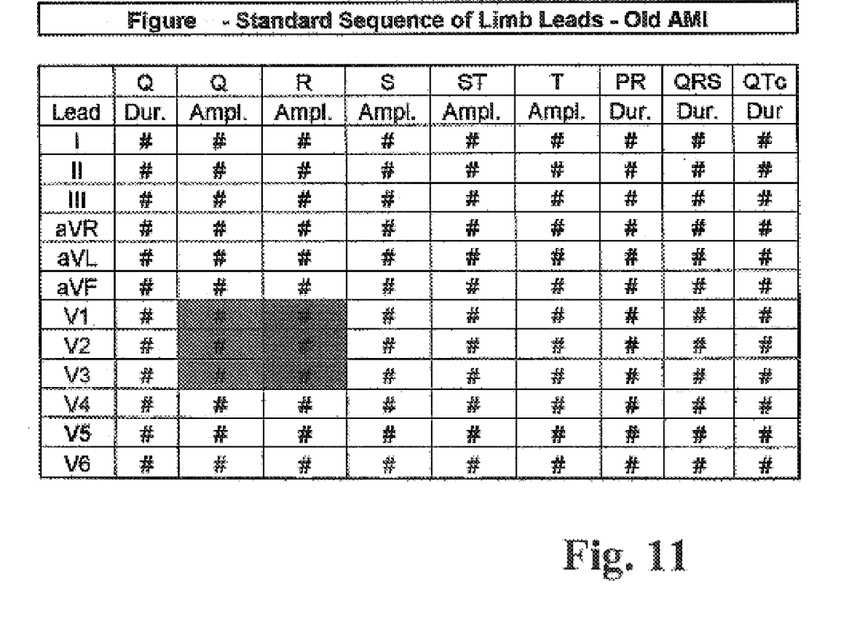

In FIG. 11, the matrix illustrated here reflects QS-complexes in leads V1, V2 and V3, without significant associated abnormalities of repolarization. This is consistent with healed anterior MI.

Figure 12:
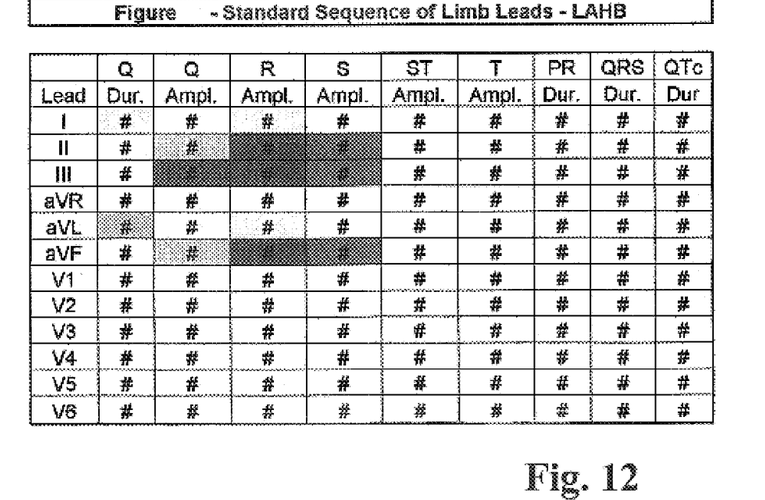

The matrix of FIG. 12 shows wider than normal Q and tall R-waves in leads I and aVL. Seen in leads II, III and aVF are smaller-than-normal R-waves, and deeper-than-normal S-waves, diminished or absent Q-waves, and abnormally low R-waves. These findings typify left anterior hemiblock.

2. Monitoring for Myocardial Ischemia

Figure 13:
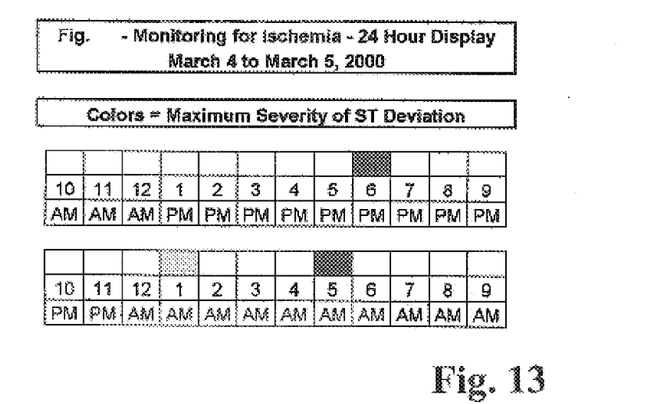
FIGS. 13 and 14 illustrate how color coding as proposed by the invention can be employed to present patient-specific ECG information in a time-line manner based upon certain time-span monitoring of that patient.
Figure 14:
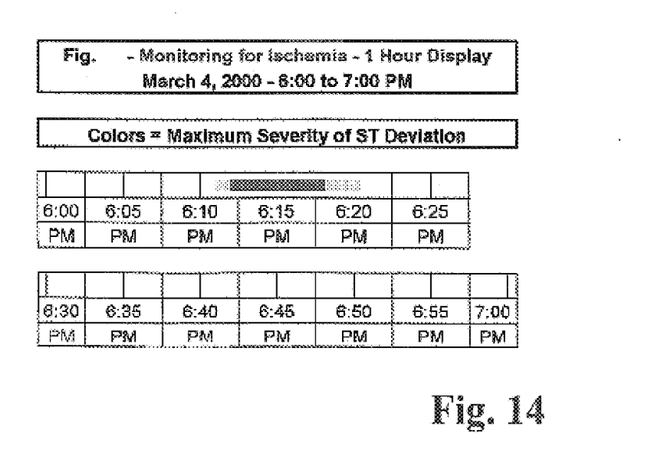

In analyzing sequentially acquired ECG data, one may choose to calculate standard-scores using not the means and standard deviations of a population of other patients, but instead, the means and standard deviations of the patient's own data, acquired during a "baseline" period. Thus, any detected changes would be in comparison to the patient's own resting ECG. The proposed technique has several important advantages over present methods of trying to detect ischemia with ambulatory monitoring, in the coronary or intensive care unit, the operating room, and during stress tests:

(1) By coloring those portions of the record that are abnormal, the technique permits rapid review of large amounts of data, and how that data relates to time. FIGS. 13 and 14 below illustrate this advantage. FIG. 13 immediately shows the reader that during 24-hours of monitoring, there were precisely 3-hours during which the patient had periods of significant depression for his or her ST-segments. FIG. 14 shows that by selecting one of those hourly periods and magnifying it, one equally rapidly sees the exact time, duration and relative severity of a specific episode of ischemia.

(2) By emphasizing the statistical significance of any apparent deviations from the baseline record, the technique permits the reader to detect those changes that are most likely to be clinically important, and less likely to be artifactual.

(3) The technique is exhaustive. In monitoring using traditional analog signals, cardiologists depend heavily on the vigilance of nurses and technicians for detecting abnormalities. This is because the cardiologist can only interpret and treat those abnormalities that a technician or nurse happens to notice and then record. When a nurse is responsible for watching many different monitor screens in a coronary care unit, or a technician must review ambulatory monitor records for several hours per day, errors of omission are common. Because the proposed method conveniently displays a great deal of data on a single screen or sheet of paper, the cardiologist can quickly review all the abnormalities that have occurred without having to rely on prior screening. This feature of the invention also permits one to incorporate a concise and meaningful report in a patient's medical record.

(4) The methodology of the present invention is quite cost-effective. For example, by eliminating the need for a technician to "screen" the data acquired during episodes of ambulatory monitoring, the method increases the efficiency, and reduces the cost, of a study.

FIG. 13 shows that the monitoring for this "representative" patient began at about 10:00 AM and persisted for 24-hours. During this period, there were 3-hour-long periods during which the patient had at least one episode of statistically significant depression of ST-segments. The most severe episode occurred between 6:00 and 7:00 PM.

FIG. 14 shows a magnified display of the above patient's record for the hour from 6:00 to 7:00 PM. What is shown is one episode of ischemia that began at 6:11 PM, which episode reached peak intensity at 6:13 PM, and lasted a total of about 10-minutes.

3. Monitoring for Arrhythmias

The same principles apply to using the methodology of this invention to monitor patients for cardiac arrhythmias. For this application, one would use pairs of simultaneously inscribed horizontal lines along with a designated time scale, e.g. 1-hour for the entire width of a page. The next pair of horizontal lines would depict the recorded events for the subsequent hour of monitoring. The upper line of each pair represents the RR-interval. Therefore, if a segment of this line shifts toward the red, it means that the RR-interval has lengthened, i.e. the cardiac rate has slowed. Conversely, if a segment of this line shifts toward the violet, it means that the RR-interval has shortened, i.e. the cardiac rate has increased. The lower line of each group represents the duration of the QRS-complex. If a segment of this line shifts toward the red, it means that the duration of the QRS has increased during that period.

Figure 15:
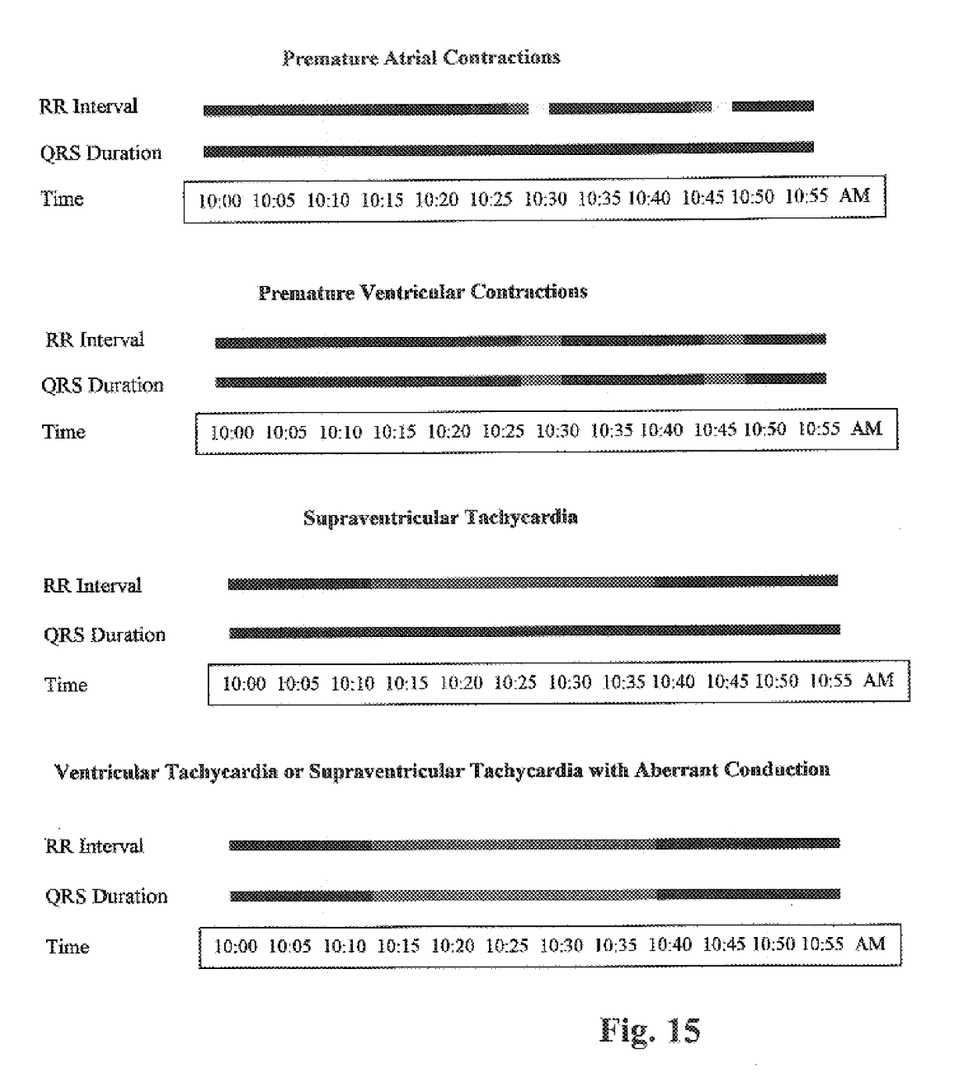
FIGS. 15, and 16 provide other illustrations of time-line presentations of time-monitoring activity with respect to which monitored events are presented visually in a color-coded fashion in accordance with implementation and practice of this invention.

FIG. 15 illustrates, in a time-based fashion, four common examples of arrhythmias. In each case, the events were recorded between 10:00 AM and 10:59 AM:

Panel A—Premature Atrial Contractions (PACs)—In each of both examples, the blue/yellow segment in the upper line show that there was a premature beat followed by a compensatory pause. The blue portion represents the short interval between the preceding sinus beat and the PAC. The yellow portion represents the incomplete compensatory pause immediately after the PAC. Since the lower line did not change color, it means that the QRS did not widen, and therefore the premature beat must have been supraventricular.

Panel B—Premature Ventricular Contractions (PVCs)—In each of both examples, the blue/red segment in the upper line shows that there was a premature beat followed by a compensatory pause that was longer than the compensatory associated with the PAC (since the $2^{nd}$ half of the segment was red, rather than yellow). The blue portion represents the short interval between the preceding sinus beat and the PVC. The red portion represents the subsequent complete compensatory typical of a PVC. Since the lower line turned red at the time of each of these events, it confirms that there was a widening of the QRS that would be typical of a PVC. The possibility of a PAC with aberrant conduction is excluded by the demonstration of the complete compensatory pause that the upper line shows.

Panel C—Supraentricular Tachycardia—The blue segment in the upper line shows that there was a prolonged episode of tachycardia. Since the lower line did not change color, there was no associated increase in the duration of the QRS. Therefore, this episode of tachycardia was supraventricular.

Panel D—Ventricular Tachycardia or Supraventricular tachycardia with Aberration—The blue segment in the upper line illustrates another prolonged episode of tachycardia. Since, in this case, the lower line turned red during this period, the episode was associated with prolongation of the QRS. Therefore, this episode of tachycardia was either ventricular or supraventricular with aberrant conduction.

Figure 16:
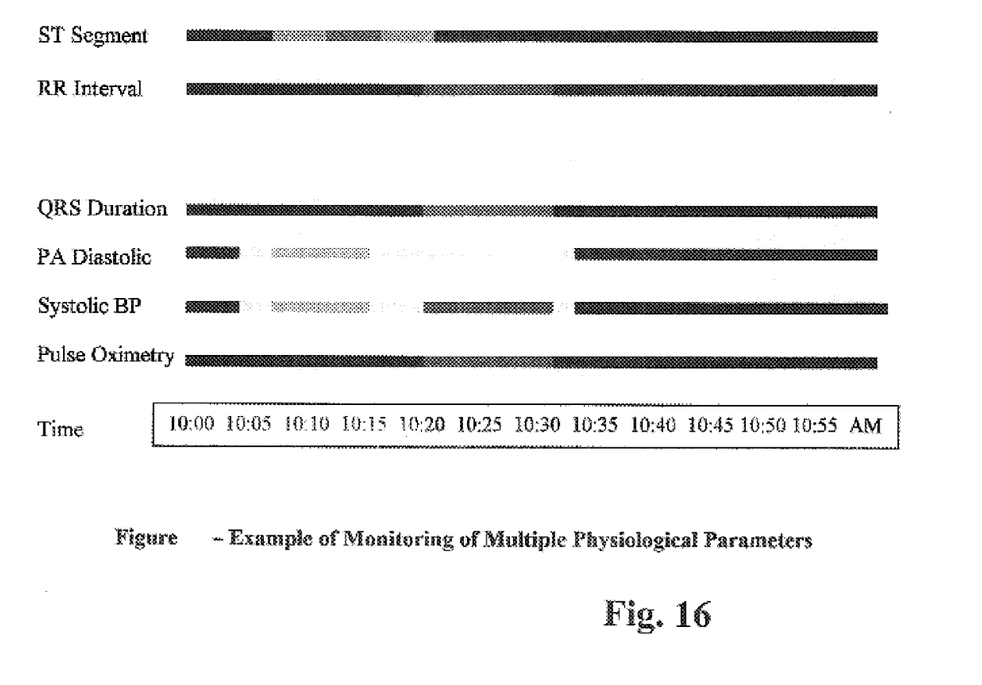

FIG. 16 illustrates, on a time basis, the simultaneous monitoring of six clinically important parameters, also between 10:00 AM and 10:59 AM. The first three panels show ECG parameters, and the last three panels reflect hemodynamic changes. In this example, the color display demonstrates changes in these six parameters before, during and after an episode of myocardial ischemia.

Panel A—There is progressively severe depression of the ST-segment followed by gradual resolution of this depression.

Panel B—There is an episode of tachycardia that begins as the depression of the ST-segment is resolving.

Panel C—Widening of the QRS during the tachycardia shows that is either ventricular tachycardia or supraventricular with aberrant conduction. Its association with the myocardial ischemia shown in Panel A, and the concomitant marked fall in systolic blood pressure demonstrated in Panel E, make ventricular tachycardia much more likely.

Panel D—The progressive rise in pulmonary arterial diastolic pressure associated with ischemia typically precedes the depression of the ST-segments. In this example, the elevation of the pulmonary arterial diastolic pressure lasts especially long because of the episode of ventricular taxchycardia.

Panel E—The systolic blood pressure increases during ischemia in most patients, and its time course parallels that of the rise in the pulmonary arterial diastolic pressure. In this example, however, the onset of the ventricular tachycardia causes an abrupt and marked fall in the systolic blood pressure.

Panel F—The sudden fall of the patient's cardiac output because of the ventricular tachycardia also causes a drop in the amount of oxygen in the patient's blood, and the pulse oximetry detects this change.

From the above detailed set of verbal, and visually referred-to drawing-figure, illustrations, the significant advantages of the structural methodology of the present invention should be quite apparent. By utilizing, as described, a selected range of colors, and by choosing an appropriate number of differentiable colors to work with, a very powerful visual communication of important, and complex cardio-ECG phenomena, singular, and interrelated, can be presented in a manner quickly interpretable.

Those possessing general skill in the art will recognize here the opportunity to introduce certain useful variations and modifications, and all of such variations and modifications are deemed to be within the scope of the present invention.

We claim:

1. A method utilizing color coding for presenting both qualitative and numeric quantitative, time-displacement comparative ECG data comprising acquiring time-based ECG data from a person, comparing such acquired data qualitatively and numerically quantitatively to ECG data present in a previously established, relevant ECG database, during said comparing, noting like regions of compared ECG data wherein certain qualitative and numeric quantitative characterizable differences appear, and following said comparing and noting steps, presenting such acquired ECG data in a manner employing differentiating color coding to identify, on a time base, certain qualitative and numeric quantitative comparative aspects of the noted, difference-characterized regions.

2. The method of claim 1, wherein said comparing and noting include implementing selected statistical analysis relative to numeric quantitative data.

3. The method of claim 1, wherein the previously established database employed during said comparing and noting steps takes the form of person-specific, previously acquired ECG data.

4. The method of claim 1, wherein the previously established database employed during said comparing and noting steps takes the form of a normalized collection of ECG data previously derived from an appropriate, relevant, selected population of people.

5. The method of claim 1, wherein said presenting takes the form of showing color-coded ECG information in a format which includes at least one of (a) a graphical wave-like format, (b) a tabular format, (c) a matrix-like format, and (d) a time-line format.

6. The method of claim 1, wherein each code color employed conveys both qualitative and quantitative comparative ECG information.

7. A system for presenting ECG data comprising
input structure for acquiring time-based ECG data from a person,
comparison structure operatively connected to said input structure, and having access to an available, previously established, relevant ECG database, operable to compare such acquired and previously established data both qualitatively and numerically quantitatively, and to note selected differences therebetween, and
color-coding and output structure, operatively connected to said comparison structure, operable selectively to assign differentiating coding colors to different regions of different noted, compared, qualitative and numeric quantitative ECG data differences, and to output, on the basis thereof, and on a time base, a color-coded visual presentation of the acquired ECG data, color-marked to identify and characterize such noted differences.

* * * * *